United States Patent
Kaneko

Patent Number: 6,076,389
Date of Patent: Jun. 20, 2000

[54] METHOD FOR JUDGING THE FAILURE OR END OF LIFE OF A SENSOR ELEMENT

[75] Inventor: Minoru Kaneko, Gunma, Japan

[73] Assignees: Akebono Brake Industry Co., Ltd., Tokyo; Akebono Research and Development Centre Ltd., Hanyu, both of Japan

[21] Appl. No.: 09/163,302

[22] Filed: Sep. 30, 1998

[30] Foreign Application Priority Data

Sep. 30, 1997 [JP] Japan ................................ 9-265501

[51] Int. Cl.[7] ................................................. F02B 33/00
[52] U.S. Cl. ........................................................... 73/1.06
[58] Field of Search ................................................ 73/1.06

[56] References Cited

U.S. PATENT DOCUMENTS 4,252,098 2/1981 Tomczak et al. .

FOREIGN PATENT DOCUMENTS 8-233770 9/1996 Japan .

*Primary Examiner*—Robert Raevis
*Attorney, Agent, or Firm*—Morgan, Lewis & Bockius LLP

[57] ABSTRACT

In the present sensor element failure or end of life judging method, the internal impedance of a gas sensor element is measured and, if the thus measured internal impedance goes beyond a previously determined threshold value, then it is judged that the gas sensor element fails or comes to the end of life.

12 Claims, 1 Drawing Sheet

SWITCHING DEVICE
CONTROL SIGNAL

SWITCHING DEVICE
CONTROL SIGNAL

METHOD FOR JUDGING THE FAILURE OR END OF LIFE OF A SENSOR ELEMENT

BACKGROUND OF THE INVENTION

1. Field of the Invention

The present invention relates to a method for judging the failure or end of life of a sensor element and, in particular, to such method which is able to judge the same with accuracy.

2. Description of the Related Art

A gas sensor element is used to detect an electromotive force generated when a chemical substance contained therein reacts with a substance to be detected to thereby measure the density of the substance to be detected and the like. As the gas sensor element is used, it will deteriorate and thus it can fail or come to the end of life.

Conventionally, as a method for judging the failure or the end of life of the sensor element due to the deterioration thereof, there are known several methods, for example, a judging method using the accumulation of the operation time of a gas sensor element as disclosed in Japanese Patent Publication No. Hei. 8-233770, a judging method using the periodical proofreading of the sensor element, and the like. However, in these conventional judging methods, there are still found some problems to be solved as follows:

(1) Judging method using the accumulation of the operation time (Japanese Patent Publication No. Hei. 8-233770): Since the operation time of the gas sensor element is accumulated and measured for judgment on the failure or end of life of the gas sensor element, the accumulated operation time must be stored, which means that it is necessary to provide a device for storing the accumulated operation time. Because the judgment is made based on the operation time of the sensor element, even if the sensor element is deteriorating at an accelerated rate, the end of life thereof cannot be judged unless enough operation time has been accumulated to obtain an effective evaluation; and, (2) Judging method using the periodical proofreading of the sensor element: In this method, the sensor element is proofread during a previously determined period using some reference source or other reference means. The deterioration of the sensor element cannot be measured during the operation period. In addition, it is necessary to prepare the reference source before proofreading the sensor element.

SUMMARY OF THE INVENTION

The present invention aims at solving the above problems found in the conventional methods for judging the degree of deterioration of the sensor element. Accordingly, it is an object of the invention to provide a method for judging the failure or end of life of a gas sensor element. Based on the fact that the internal impedance of the gas sensor element varies as the gas sensor element deteriorates, the system monitors variations in the internal impedance of the gas sensor element to thereby detect the deterioration of the gas sensor element easily and accurately.

In particular, the internal impedance of the gas sensor element varies with the passage of time in such a manner as shown in FIG. 1. That is, based on the variations of the measured internal impedance of the gas sensor element linked with the operation time of the gas sensor element, the present method monitors the variations in the internal impedance of the gas sensor element and compares them with a previously determined value to thereby detect the failure or end of life of the gas sensor element.

As to the previously determined value for judgment of the failure or end of life of the gas sensor element, if a plurality of previously determined values are prepared and stored in a measuring system, then not only the contents of the failure can be subdivided and displayed but also the remaining time up to the end of life can be previously obtained through the estimated calculation.

Also, since the remaining time up to the end of life of the sensor element can be estimated, the proper maintenance and contort of the sensor element are possible.

In attaining the above object, according to the invention, as technical means for solving the problems, there is employed a method for judging the failure or end of life of a gas sensor element, in which the internal impedance of the gas sensor element is measured and, if the measured value of the internal impedance goes beyond a previously determined threshold value, then it is judged that the gas sensor element fails or comes to the end of life thereof.

DETAILED DESCRIPTION OF THE PREFERRED EMBODIMENTS

Now, description will be given below in detail of an embodiment of a method for judging the failure or end of life of a gas sensor element according to the invention with reference to the accompanying drawings. In particular, FIG. 2 is a block diagram of the structure of a system for judging the failure or end of life of a gas sensor element.

Figure 2:
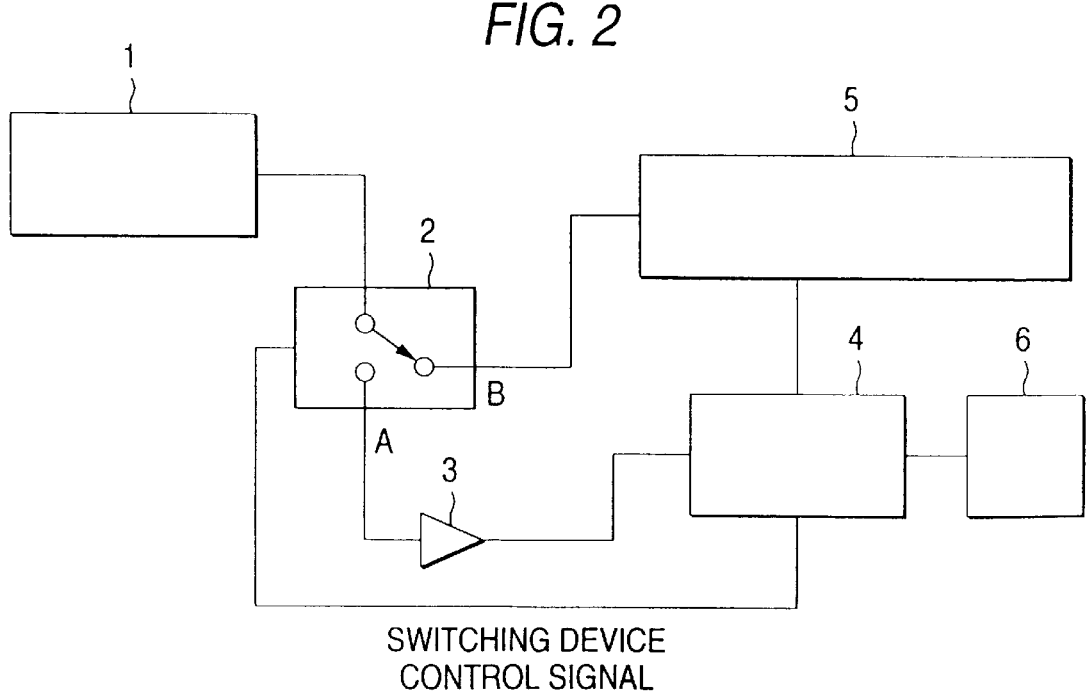
FIG. 2 is a block diagram of the structure of a system used to judge the gas sensor element for failure or end of life.

In FIG. 2, reference character 1 designates a gas sensor element used as an element to be detected which is judged for the failure thereof or the end of life thereof. In particular, the gas sensor element 1 is judged for the failure thereof or the end of life thereof by the illustrated system structure that comprises a switching device 2, an amplifier 3, a CPU 4 for computation, an internal impedance measuring circuit 5 and a display part 6.

The switching device 2 is controlled by the CPU 4: that is, when it is in normal operation, the switching device 2 is switched over to a first output terminal A to thereby measure the density of gas; and, when judging the failure or end of life of the gas sensor element, the switching device 2 can be switched over to a second output terminal B.

Due to use of the switching device 2, the output terminal of the gas sensor element 1 can be used in common, as a normal measuring terminal and as an internal impedance measuring terminal. As a result, the number of output terminals needed for the gas sensor element 1 are reduced in the present embodiment.

The first output terminal A of the switching device 2 is connected to the amplifier 3 and, further, the output of the amplifier 3 is A/D converted and is then input to the CPU 4 for computation.

Also, the second output terminal B of the switching device 2 is connected to the internal impedance measuring circuit 5 and, further, the output of the internal impedance measuring circuit 5 is A/D converted and is then input to the CPU 4 for computation.

And, the output terminal of the CPU 4 for computation is connected to the display part 6.

By use of the above-structured system, the judgment of the failure of the gas sensor element, the judgment of the deterioration of the gas sensor element and the judgment of the end of life of the gas sensor element are executed in the following manner:

That is, the judgment of the gas sensor element is executed when at least one of the following conditions occur: that is, a) when the power source of a measuring system is put to work (confirmation of a start time); b) each time the operation time of the sensor element goes beyond a given time (periodical confirmation); and c) when the failure confirmation of the sensor element is requested by a user (non-periodical confirmation).

If at least one of the above-mentioned conditions, that is, a), b), and c) occur and the present system is put into its failure judging operation, then the CPU 4 switches the switching device 2 over to the second output terminal B to thereby connect the output of the gas sensor element to the internal impedance measuring circuit 5.

Figure 1:
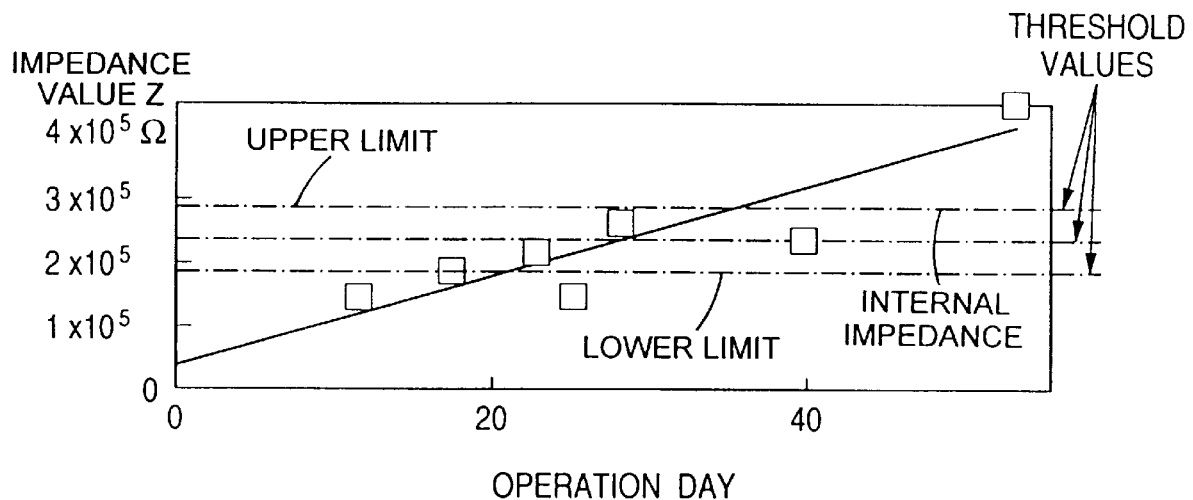
FIG. 1 is a graphical representation of the relation between the internal impedance and operation days of a gas sensor element.

In response to this, the internal impedance measuring circuit 5 measures the internal impedance of the gas sensor element that is viewed from the output terminal thereof, and outputs the measured result to the CPU. Then, the CPU, after it waits for a given time, compares the internal impedance measured value of the gas sensor element with a plurality of previously determined failure judging values (threshold values) in accordance with a map which is previously stored within the CPU and as is shown in FIG. 1, thereby judging or checking the gas sensor element for the failure thereof.

If the gas sensor element is judged that it fails, then a display to that effect is made on the display part.

On the other hand, if the gas sensor element is not judged that it fails or comes to the end of life, then the failure judging operation is ended; and, the switching device 2 is switched over to the first output terminal A thereof and is thereby put into its normal operation.

Conditions for judging the deterioration or end of life of the gas sensor element:

Judgment on the deterioration or end of life of the gas sensor element is also made similarly to the above-mentioned failure judging operation by switching the switching device over to the second output terminal B thereof and measuring the internal impedance of the gas sensor element. If the measured internal impedance is found in any one of the following conditions, then the gas sensor element is judged that it deteriorates or comes to the end of life:

1) If the measured value of the internal impedance of the gas sensor element goes beyond, for example, the preset upper limit threshold value shown in FIG. 1, then it is judged that the gas sensor element comes to the end of life;

2) If the measured value of the internal impedance of the gas sensor element goes below the preset lower limit threshold value, then it is judged that the gas sensor element deteriorates; and, 3) If the measured value of the internal impedance of the gas sensor element shows 0Ω, then it is judged that the gas sensor element short-circuits, that is, it fails.

Therefore, "comes to the end of life" is defined as a gas sensor with a measured internal impedance above the preset upper limit. The "deterioration" of the gas sensor element is defined as an internal impedance below the preset lower limit. "Failure" is defined as a gas sensor with a measured internal impedance of 0Ω.

Method for displaying the remaining life time of the gas sensor element:

The remaining life time of the gas sensor element is measured in the following manner and the measured result is displayed on the display device.

In particular, the internal impedance of the gas sensor element is measured according to the above-mentioned method and, based on the measured value, the remaining time up to the end of life of the gas sensor element is then measured.

For example, in FIG. 1, in accordance with an experimentally obtained graph, the relation between the internal impedance of the gas sensor element and the operable days D up to the end of life thereof is expressed in a numerical formula:

$$D=(Z-K_1)/K_2 \quad (1)$$

where D expresses the operable days, Z expresses the internal impedance for judgment of the end of life of the gas sensor element, and $K_1$, $K_2$ are respectively constants. For example, if the internal impedance (Z) for a given gas sensor element is $3 \times 10^5$ Ω, then this value is applied to Equation 1 to determine the operable days before it must be replaced or initial estimated life of the sensor.

From the above formula, the remaining operable days Dr up to the end of life of the sensor element can be obtained according to the following formula (2) using the current internal impedance of the gas sensor element:

$$Dr=D-(Z_0-K_1)/K_2 \quad (2)$$

where $Z_0$ expresses the current internal impedance of the gas sensor element. For example, if the operable days (D) was calculated to be 60 days for a given sensor, and the current internal impedance ($Z_0$) of the same gas sensor is measured to be $2 \times 10^5$Ω, those values are applied to Equation 2 to determine the remaining operable days of the sensor from the operable days (D).

That is, if the internal impedance characteristic of the gas sensor element is previously obtained through calculation based on experiments or theoretical models in the above-mentioned manner and is then stored in the CPU as a program, then the remaining life of the gas sensor element can be confirmed easily, which makes it possible to maintain and control the gas sensor element properly.

As has been described heretofore in detail, according to the invention, due to the fact that the variations in the internal impedance of the gas sensor element are monitored and are compared with the previously determined values, the failure of the gas sensor element or the end of life thereof can be detected accurately. Also, since a plurality of values are prepared for judgment of the failure of the gas sensor element or the end of life thereof, not only the contents of the failure can be subdivided and displayed, but also the remaining time up to the end of life of the gas sensor element can be estimated and calculated. As a result of this, there can be provided several excellent effects: for example, the maintenance and control of the gas sensor element can be carried out properly.

What is claimed is:

1. A method of determining the life of a gas sensor element, comprising the steps of:

measuring an internal impedance of the gas sensor element to obtain a measured value; and comparing the measured value of the internal impedance with a previously determined upper limit threshold value; and calculating the life of the gas sensor element, wherein an end of the life of the gas sensor element is determined when the measured value exceeds the upper limit threshold value.

2. The method of determining according to claim 1, further comprising the step of displaying the measured value.

3. The method of determining according to claim 1, further comprising the step of displaying the threshold value.

4. The method of determining according to claim 1, further comprising the step of displaying the life of the gas sensor element.

5. The method of determining according to claim 1, further including the step of comparing the measured value with a lower limit threshold value.

6. The method of determining according to claim 5, wherein the step of calculating the life further includes determining a deteriorated life of the gas sensor element when the measured value is less than the lower limit threshold value.

7. The method of determining according to claim 6, further comprising the step of displaying the upper and lower limit threshold values.

8. The method of determining according to claim 1, further comprising the step of switching a device at least between two connections, wherein a first contact engages the gas sensor element with an internal impedance measuring circuit and a second contact engages the gas sensor element for performance of a running computation.

9. The method of determining according to claim 8, further comprising the step of displaying results from the internal impedance measuring circuit when the first contact is engaged and displaying results from the running computation when the second contact is engaged.

10. A method of judging the end of life of a gas sensor element, comprising the steps of:

measuring a internal impedance of the gas sensor element to obtain a measured value;

estimating the end of life of the gas sensor element by comparing the measured value of the internal impedance with a predetermined value calculated from a prior internal impedance value; and calculating a remaining operable time of the gas sensor element based on the estimated end of the life thereof.

11. The method of judging according to claim 10, further comprising the step of displaying the remaining operable time.

12. A method of evaluating the life of a gas sensor element, comprising the steps of:

providing a gas sensor element with an output terminal for displaying an electromotive force and an internal impedance;

measuring an internal impedance of the gas sensor element to obtain a measured value; and calculating the life of the gas sensor element from the measured value.

* * * * *